US009969707B2

(12) United States Patent
Savard et al.

(10) Patent No.: US 9,969,707 B2
(45) Date of Patent: May 15, 2018

(54) METHOD FOR EXTRACTING ANTHOCYANIN DERIVATIVES FROM A PLANT SOURCE

(71) Applicant: Centre de Recherche Industrielle du Québec, Québec (CA)

(72) Inventors: Sylvain Savard, L'Ancienne Lorette (CA); André Tremblay, Québec (CA); Michel Arsenault, Lévis (CA)

(*) Notice: Subject to any disclaimer, the term of this patent is extended or adjusted under 35 U.S.C. 154(b) by 0 days. days.

(21) Appl. No.: 14/362,824

(22) PCT Filed: Dec. 14, 2012

(86) PCT No.: PCT/CA2012/001154
§ 371 (c)(1),
(2) Date: Jun. 4, 2014

(87) PCT Pub. No.: WO2013/086621
PCT Pub. Date: Jun. 20, 2013

(65) Prior Publication Data
US 2014/0309439 A1    Oct. 16, 2014

Related U.S. Application Data

(60) Provisional application No. 61/576,591, filed on Dec. 16, 2011.

(51) Int. Cl.
*A61K 36/45* (2006.01)
*C07D 311/62* (2006.01)
*C07H 17/065* (2006.01)

(52) U.S. Cl.
CPC .......... *C07D 311/62* (2013.01); *C07H 17/065* (2013.01); *A61K 36/45* (2013.01)

(58) Field of Classification Search
CPC ............................. A61K 36/45; C07D 311/62
See application file for complete search history.

(56) References Cited

U.S. PATENT DOCUMENTS

| 5,525,341 | A | 6/1996 | Walker et al. |
| 5,646,178 | A | 7/1997 | Walker et al. |
| 6,461,648 | B2 | 10/2002 | Soulier et al. |
| 6,960,360 | B2 | 11/2005 | Gourdin et al. |
| 7,208,181 | B1 | 4/2007 | King et al. |
| 7,306,815 | B2 | 12/2007 | Gourdin et al. |
| 7,462,370 | B2 | 12/2008 | Bailey et al. |
| 7,682,637 | B2 | 3/2010 | Gourdin et al. |
| 7,820,207 | B2 | 10/2010 | Eidenberger |
| 7,939,111 | B2 | 5/2011 | Cheng et al. |
| 2002/0114853 | A1 | 8/2002 | Krasutsky et al. |
| 2003/0203962 | A1 | 10/2003 | Howell et al. |
| 2004/0009242 | A1 | 1/2004 | Krasutsky et al. |
| 2004/0109905 | A1 | 6/2004 | Bagchi |
| 2004/0156925 | A1 | 8/2004 | Soulier et al. |
| 2005/0037130 | A1 | 2/2005 | Nair |
| 2006/0280816 | A1 | 12/2006 | Gourdin et al. |
| 2007/0292539 | A1 | 12/2007 | Vorsa et al. |
| 2008/0255226 | A1 | 10/2008 | Eidenberger |
| 2009/0176718 | A1 | 7/2009 | Ribnicky et al. |
| 2009/0258940 | A1 | 10/2009 | Besnard et al. |
| 2009/0318377 | A1 | 12/2009 | Vezina et al. |
| 2011/0059193 | A1 | 3/2011 | Tournay et al. |
| 2011/0117221 | A1 | 5/2011 | Eidenberger |
| 2011/0206794 | A1* | 8/2011 | O'Kennedy ........... A61K 36/81 424/777 |

FOREIGN PATENT DOCUMENTS

| CA | 2359475 A1 | 8/2000 |
| CA | 2371896 A1 | 12/2001 |
| CA | 2506651 A1 | 6/2004 |
| CA | 2554182 A1 | 8/2005 |
| CA | 2546138 A1 | 11/2006 |
| CA | 2735343 A1 | 4/2011 |
| CA | 2421109 C | 5/2011 |
| CN | 1517343 | 8/2004 |
| CN | 1583774 | 2/2005 |
| CN | 100560579 A1 | 11/2007 |
| CN | 101215424 | 7/2008 |
| CN | 101265252 | 9/2008 |
| CN | 101775417 | 7/2010 |
| EP | 0412300 B1 | 11/1995 |

(Continued)

OTHER PUBLICATIONS

Kataoka et al., caplus 1936:3371 (1936).*
Derivative, 2015, https://en.wikipedia.org/wiki/Derivative_(chemistry).*
PercentageWater, 2017, http://www.livestrong.com/article/350652-percentage-of-water-in-fruits-vegetables/.*
Barnes et al., Journal of ChromatographyA 2009, 1216 (23), 4728-4735.*
English abstract of CN100560579, Published Nov. 28, 2007, retrieved from the Internet: http://worldwide.espacenet.com.
English abstract of CN1517343, Published Aug. 4, 2004, Retrieved from the Internet: http://worldwide.espacenet.com.
English abstract of CN1583774, Published Feb. 23, 2005, Retrieved from the Internet: http://worldwide.espacenet.com.
English abstract of CN101215424, Published Jul. 9, 2008, Retrieved from the Internet: http://worldwide.espacenet.com.
English abstract of CN101265252, Published Sep. 17, 2008, Retrieved from the Internet: http://worldwide.espacenet.com.
English abstract of CN101775417, Published Jul. 14, 2010, Retrieved from the internet: http://worldwide.espacenet.com.
English abstract of CN100560579, Published Nov. 18, 2008 Retrieved from the Internet: http://worldwide.espacenet.com.
English abstract of FR2641283, Published Jul. 6, 1990, Retrieved from the internet: http://worldwide.espacenet.com.
Fuleki et al. "Quantitative Methods for Anthocyanins. 2. Determination of Total Anthocyanin and Degradation Index for Cranberry Juice", Journal of Food Science, vol. 33, 1968, pp. 78-83.
Wrolstad, R.E. "Anthocyanins", Natural Food Colorants. Science and Technology, 2000, pp. 237-252.

(Continued)

*Primary Examiner* — Sun Jae Yoo
(74) *Attorney, Agent, or Firm* — Benoit & Cote Inc.; Mathieu Miron

(57) ABSTRACT

The present document describes a method for extracting anthocyanin derivatives from a plant source. The method comprises the step of separating a homogenized extract of plant source in a polar acidified solvent for obtaining a residual solid, and a filtrate mixed with the acidified polar solvent. The separation includes a coarse filtration done by centrifugation of the plant source extract, by a filtration with a first filter having a pore size of about 100 µm, and a fine filtration is done using a second filter having a pore size of about 10 µm. Then, the filtrate mixed with the acidified polar solvent is evaporated for substantially separating the acidified polar solvent from the filtrate to obtain a semi-solid extract of anthocyanin derivatives.

33 Claims, 2 Drawing Sheets

(56) References Cited

FOREIGN PATENT DOCUMENTS

| EP | 1443948 B1 | 6/2005 |
|---|---|---|
| FR | 2641283 A1 | 7/1990 |
| WO | 200033670 | 6/2000 |
| WO | 0217732 A2 | 3/2002 |
| WO | 2007125562 A2 | 11/2007 |
| WO | 2009031051 A2 | 3/2009 |
| WO | 2009059218 A1 | 5/2009 |

OTHER PUBLICATIONS

Kalt et al. "Anthocyanins, Phenolics, and Antioxidant Capacity of Processed Lowbush Blueberry Products", Journal of Food Science, vol. 65, No. 3, 2000, pp. 390-393.

Lee et al."Extraction of Anthocyanins and Polyphenolics from Blueberry Processing Waste", Journal of Food Science, vol. 69, No. 7, 2004, pp. 564-573.

International Search Report.

Nicoue et al. Journal of Agricultural Food and Chemistry. Wild Blueberries of Quebec: Extraction and Identification, 2007, vol. 55, issue 14, pp. 5626-5635.

Written Opinion.

Barnes et al "General method for extraction of blueberry anthocyanins and identification using high performance liquid chromatography-electrospray ionization-ion trap-time of flight-mass spectrometry", J. of Chromatography A, 2009, vol. 1216, No. 23, pp. 4728-4735.

Lapornik et al. "Comparison of extracts prepared from plant by-products using different solvents and extraction time", J. of Food Engineering, 2005, vol. 71, No. 2, pp. 214-222.

Cacace and al. "Optimization of Extraction of Anthocyanins from Black Currants with Aqueous Ethanol", J. of Food Science, 2003, vol. 68, No. 1, pp. 240-248.

Segura-Carretero et al. "Selective extraction, separation, and identification of anthocyanins from *Hibiscus sabdariffa* L. using solid phase extraction-capillary electrophoresis-mass spectrometry (time-of-flight/ion trap)", Electrophoresis, 2008, vol. 29, No. 13, pp. 2852-2861.

He et al. "High-purity isolation of anthocyanins mixture from fruits and vegetables a novel solid-phase extraction method using mixed mode cation-exchange chromatography", J. of Chromatography A, 2011, vol. 1218, pp. 7914-7922.

Supplementary European Search Report of corresponding European application No. 12857528. 9; Munich; Daniela Gavriliu.

\* cited by examiner

METHOD FOR EXTRACTING ANTHOCYANIN DERIVATIVES FROM A PLANT SOURCE

CROSS-REFERENCE TO RELATED APPLICATIONS

This application is a U.S. national phase of International Application under 35 USC § 371 of PCT/CA2012/001154, filed Dec. 14, 2012, which claims priority from and the benefit under 35 USC 119(e) of US provisional patent application 61/576,591, filed on Dec. 16, 2012, the specification of which is hereby incorporated by reference, in its entirety.

BACKGROUND (a) Field

The subject matter disclosed generally relates to a method for extracting anthocyanin derivatives. More particularly, the subject matter generally relates to a method for extracting anthocyanin derivatives from a plant source such as blueberries.

(b) Related Prior Art

Anthocyanins are water-soluble vacuolar pigments that may appear red, purple, or blue according to their pH. They belong to a parent class of molecules called flavonoids synthesized via the phenylpropanoid pathway. They are odorless and nearly flavorless, contributing to taste as a moderately astringent sensation. Anthocyanins occur in all tissues of higher plants, including leaves, stems, roots, flowers, and fruits. Anthocyanins are derivatives of anthocyanidins which include pendant sugars.

In flowers, bright reds and purples are adaptive for attracting pollinators. In fruits, the colorful skins also attract the attention of animals, which may eat the fruits and disperse the seeds. In photosynthetic tissues (such as leaves and sometimes stems), anthocyanins have been shown to act as a "sunscreen", protecting cells from high-light damage by absorbing blue-green and UV light, thereby protecting the tissues from photoinhibition, or high-light stress. This has been shown to occur in red juvenile leaves, autumn leaves, and broad-leaved evergreen leaves that turn red during the winter. It has also been proposed that red coloration of leaves may camouflage leaves from herbivores blind to red wavelengths, or signal unpalatability, since anthocyanin synthesis often coincides with synthesis of unpalatable phenolic compounds.

In addition to their role as light-attenuators, anthocyanins also act as powerful antioxidants. However, it is not clear as to whether anthocyanins can significantly contribute to scavenging of free-radicals produced through metabolic processes in leaves, since they are located in the vacuole and, thus, spatially separated from metabolic reactive oxygen species. Some studies have shown that hydrogen peroxide produced in other organelles can be neutralized by vacuolar anthocyanin.

Anthocyanins are found in the cell vacuole, mostly in flowers and fruits but also in leaves, stems, and roots. In these parts, they are found predominantly in outer cell layers such as the epidermis and peripheral mesophyll cells.

Most frequent in nature are the glycosides of cyanidin, delphinidin, malvidin, pelargonidin, peonidin, and petunidin. Roughly 2% of all hydrocarbons fixated in photosynthesis are converted into flavonoids and their derivatives such as the anthocyanins. There is no less than $10^9$ tons of anthocyanins produced in nature per year. Not all land plants contain anthocyanin; in the Caryophyllales (including cactus, beets, and amaranth), they are replaced by betalains. However, anthocyanins and betalains have never been found in the same plant.

Plants rich in anthocyanins are *Vaccinium* species, such as blueberry, cranberry and bilberry, *Rubus* berries including black raspberry, red raspberry and blackberry, blackcurrant, cherry, eggplant peel, black rice, Concord grape and muscadine grape, red cabbage, and violet petals. Anthocyanins are less abundant in banana, asparagus, pea, fennel, pear, and potato, and may be totally absent in certain cultivars of green gooseberries.

Nature, primitive agriculture, and plant breeding have produced various uncommon crops containing anthocyanins, including blue- or red-flesh potatoes and purple or red broccoli, cabbage, cauliflower, carrots, and corn. Tomatoes have been bred conventionally for high anthocyanin content by crossing wild relatives with the common tomato to transfer a gene called the anthocyanin fruit tomato ("aft") gene into a larger and more palatable fruit.

Tomatoes have also been genetically modified with transcription factors from snapdragons to produce high levels of anthocyanins in the fruits. Anthocyanins can also be found in naturally ripened olives, and are partly responsible for the red and purple colors of some olives.

Anthocyanins are considered secondary metabolites as a food additive with E number E163 (INS number 163); they are approved for use as a food additive in the EU, Australia and New Zealand.

Richly concentrated as pigments in berries, anthocyanins were the topics of research presented at a 2007 symposium on health benefits that may result from berry consumption. Laboratory-based evidence was provided for potential health effects against: cancer; aging and neurological diseases; inflammation; diabetes; and bacterial infections.

Cancer research on anthocyanins is the most advanced, where black raspberry (*Rubus occidentalis* L.) preparations were first used to inhibit chemically induced cancer of the rat esophagus by 30-60% and of the colon by up to 80%. Effective at both the initiation and promotion/progression stages of tumor development, black raspberries are a practical research tool and a promising therapeutic source, as they contain the richest contents of anthocyanins among native North American *Rubus* berries.

Work on laboratory cancer models has shown that black raspberry anthocyanins inhibit promotion and progression of tumor cells by: stalling growth of pre-malignant cells; accelerating the rate of cell turnover, called apoptosis, effectively making the cancer cells die faster; reducing inflammatory mediators that initiate tumor onset; inhibiting growth of new blood vessels that nourish tumors, a process called angiogenesis; and minimizing cancer-induced DNA damage.

On a molecular level, berry anthocyanins were shown to turn off genes involved with proliferation, inflammation and angiogenesis, while switching on apoptosis.

In 2007, black raspberry studies entered the next pivotal level of research—the human clinical trial—for which several approved studies are underway to examine anti-cancer effects of black raspberries and cranberries on tumors in the esophagus, prostate and colon. A growing body of evidence suggests that anthocyanins and anthocyanidins may possess analgesic properties in addition to neuroprotective and anti-inflammatory activities.

Many methods have been studied in the past to obtain anthocyanin derivatives. Some known methods of anthocyanin extraction to obtain high extraction yields in terms of weight of recovered anthocyanin compared to weight of anthocyanin present in the source matter. However, those methods generally do not provide an optimal control on the purity level of the anthocyanin extracts obtained.

There is therefore a need to provide an improved method for extracting and purifying anthocyanin derivatives, and more particularly, there is a need to provide an improved method for extracting and purifying anthocyanin derivatives from a plant source such as blueberries.

SUMMARY

According to an embodiment, there is provided a method for extracting anthocyanin derivatives from a plant source, comprising the steps of:
i) separating an homogenized extract of said plant source in a polar solvent for obtaining a residual solid, and a filtrate mixed with said polar solvent; and
ii) substantially separating said polar solvent from said filtrate to obtain a semi-solid extract of anthocyanin derivatives.

The polar solvent may be acidified.

The step i) may include a coarse filtration chosen from:
by centrifugation of the plant source extract,
by a filtration with a first filter, or
a combination thereof.

The step ii) may be performed by evaporating the filtrate mixed with the polar solvent of step i).

The evaporating may be performed under reduced pressure.

The step i) may further include a fine filtration performed by a second filter.

The method may be further comprising an anthocyanin derivatives purification step iii):
iii) performing a solid phase extraction of the semi-solid extract of step ii) with an adsorbent material and an elution solvent to adsorb the anthocyanin derivatives present in the semi-solid extract on the adsorbent material.

The method may be further comprising step iv):
iv) eluting the adsorbed anthocyanin derivatives of step iii) from the adsorbent material for recovering the purified anthocyanin derivatives.

The plant source may be a source of *vaccinium* fruit.

The step i) may be performed with a first filter having a pore size of about 100 μm, and a second filter having a pore size of about 10 μm.

The adsorbent material may be chosen from C-18 silica gel or C-8 silica gel.

The homogenized extract may be obtained by mixing and pulverizing the plant source in said polar solvent.

The step iii) may include washing the adsorbent material with the elution solvent for eluting sugars and inorganic substances from the extract.

The step iii) may further include washing the adsorbent material with a second elution solvent for eluting waxes and fatty substances from the extract.

The step iii) may further includes washing the adsorbent material with a third elution solvent for eluting neutral flavonoids from the extract.

The polar solvent may be chosen from ethanol, methanol, ethyl acetate, water, acetone, butanol or combinations thereof.

The polar solvent may further comprise an acid chosen from phosphoric acid, HCl or combinations thereof.

The polar solvent may be 95% ethanol acidified with phosphoric acid.

The homogenized extract may be obtained at a temperature from about 6° C. to an ebullition temperature of the polar solvent while agitating at between about 200 and to about 3000 RPM.

The method may be further comprising a step prior to step i) of cooling the extract before the separating.

The step ii) may comprise a vacuum pressure evaporation process.

The vacuum pressure evaporation process may operate at an evaporation temperature inferior to the ebullition temperature of the polar solvent.

The eluting of the semi-solid extract may be with an elution solvent chosen from water, ethanol, methanol, demineralized water, hexane, ethyl acetate or a combination thereof.

The method may be further comprising a step prior to step iii) of dissolving in water the semi-solid extract and filtrating the semi-solid extract dissolved in water.

The C-18 adsorbent silica gel may have a particle distribution of about 40 to about 63 μm.

The C-18 adsorbent silica gel may have an organic charge of about 0.38 mmol/g.

The C-18 adsorbent silica gel may have a carbon charge of about 9.16%.

The ratio C-18 adsorbent silica gel/extract may be about 2.5:1.

The method may be further comprising a step prior to step iii) of conditioning the C-18 adsorbent silica gel by eluting 95% ethanol and then with demineralized water.

The eluting may be performed with gravity or under an external pressure.

The residence time of said extract on said gel in step iv) may be between 1 hour and 3 hour.

The recovering of the anthocyanin derivatives may be with an elution solution of about 95% ethanol in water or a gradient from 30% ethanol in water to 95% ethanol in water.

The method may be further comprising combining the first, the second and the third solutions and evaporating the acidified polar solvent.

The elution solvent may be water.

The second elution solvent may be hexane.

The third elution solvent may be ethyl acetate.

The ratio C-18 adsorbent silica gel/extract may be from about 1:1 to about 10:1.

The ratio adsorbent material/extract may be from about 1:1 to about 10:1.

According to another embodiment, there is provided a method for extracting and purifying anthocyanin derivatives from a plant source, comprising the steps of:
i) separating an homogenized extract of the plant source in a polar acidified solvent for obtaining a residual solid, and a filtrate mixed with the acidified polar solvent;
ii) evaporating under reduced pressure the filtrate mixed with the acidified polar solvent of step i) for substantially separating the acidified polar solvent from the filtrate to obtain a semi-solid extract of anthocyanin derivatives;
iii) performing a solid phase extraction of the semi-solid extract of step ii) with an adsorbent material and an elution solvent to adsorb the anthocyanin derivatives present in the semi-solid extract on the adsorbent material; and
iv) eluting the adsorbed anthocyanin derivatives of step iii) from the adsorbent material for recovering the purified anthocyanin derivatives.

The step i) may include a coarse filtration chosen from:
by centrifugation of the plant source extract,
by a filtration with a first filter, or
a combination thereof.

The step i) may further include a fine filtration performed by a second filter.

The step i) may be performed with a first filter having a pore size of about 100 μm, and a second filter having a pore size of about 10 μm.

According to another embodiment, there is provided a method for extracting anthocyanin derivatives from a filtrate mixed with a polar solvent used for separating an homogenized extract of a plant source into said filtrate and a residual solid, said method comprising the step of substantially separating said polar solvent from said filtrate to obtain a semi-solid extract of anthocyanin derivatives.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION OF THE PREFERRED EMBODIMENTS

Figure 1:
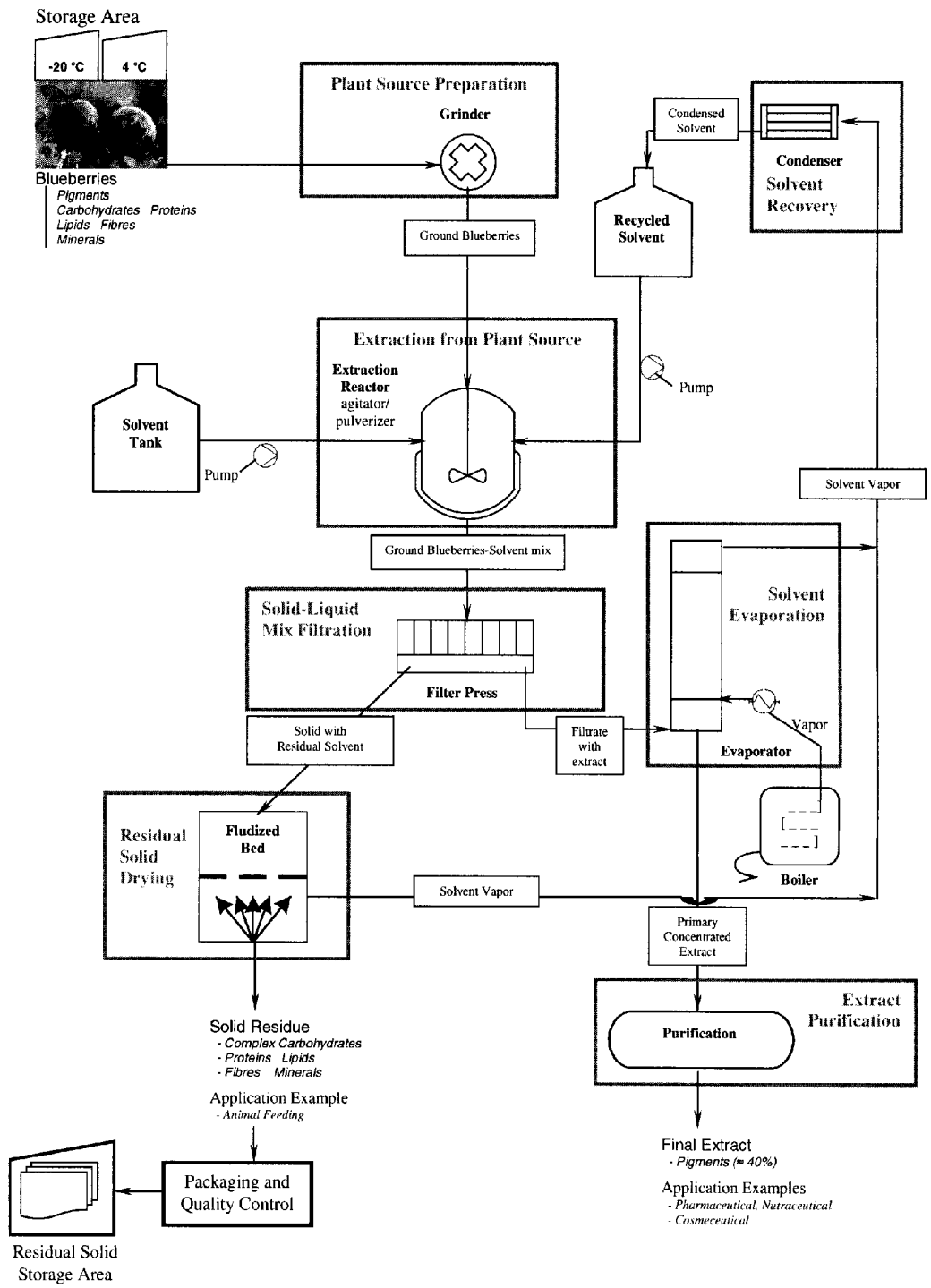
FIG. 1 illustrates an exemplary implementation of the proposed method for extracting and purifying anthocyanin derivatives from wild blueberries as a plant source, particularly showing a sequence of extraction steps, including the plant source preparation, the extraction of the plant source, the solid-liquid mix filtration, residual solid drying, solvent evaporation, extract purification, to obtain a final extract.
Figure 2:
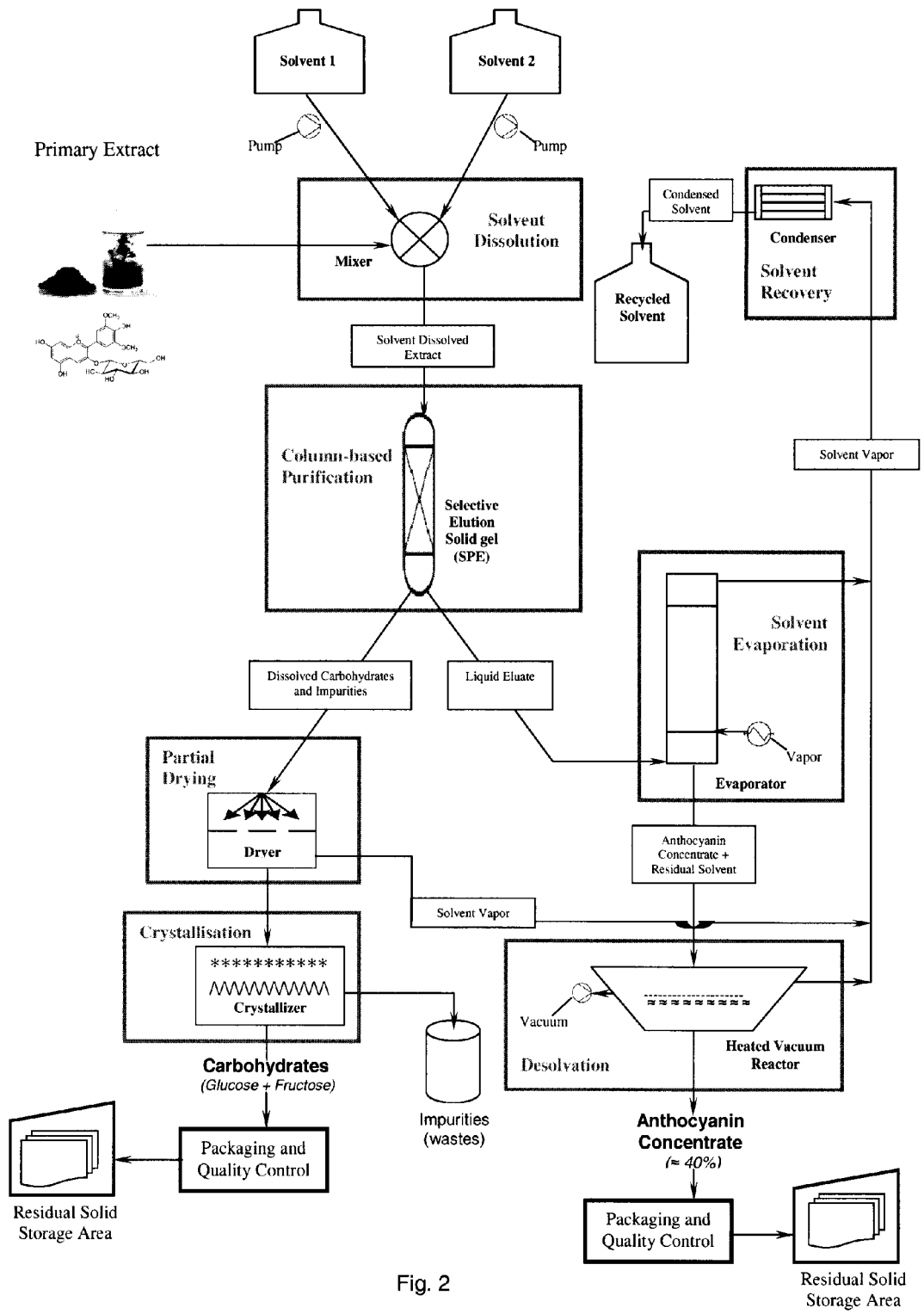
FIG. 2 illustrates an exemplary sequence of purification steps that can be performed from the primary extract as obtained by carrying out the sequence of extraction steps of FIG. 1. The steps include dissolution of the primary extract in solvent, column-based purification, partial drying, solvent evaporation, crystallization (to obtain carbohydrates), and desolvation (to obtain an anthocyanin concentrate).

There is provided a method for extracting anthocyanin derivatives from a plant source comprising the steps of:
i) separating an homogenized extract of a plant source in a polar solvent for obtaining a residual solid, and a filtrate mixed with the polar solvent, and
ii) substantially separating the polar solvent from the filtrate for obtaining a semi-solid extract of anthocyanin derivatives.

According to an embodiment, the polar solvent may be acidified. Preferably, the polar solvent may be acidified with phosphoric acid, HCl or combinations thereof.

According to another embodiment, step i) may include a coarse filtration which may be done by centrifugation of the plant source. In another embodiment, the coarse filtration may be done with a first filter, or a combination of centrifugation and a first filter.

According to another embodiment, step i) may further include a fine filtration which is performed by a second filter. According to another embodiment, the coarse filtration may be done by a two stage filtration with a first filter having a pore size of about 100 μm, and a second filter having a pore size of about 10 μm. According to another embodiment, the two methods may be combined.

The homogenized extract may be obtained by performing the homogenization at a temperature between about 6° C. to about the ebullition temperature of the polar acidified solvent. The homogenization may be performed by agitating at between about 200 RPM to about 3000 RPM.

According to an embodiment, the method may also comprise step iii), which is an anthocyanin derivatives purification step:
iii) performing a solid phase extraction of the semi-solid extract of step ii) with an adsorbent material and an elution solvent to adsorb the anthocyanin derivatives present in the semi-solid extract on the adsorbent material;

According to an embodiment, the method may also comprise step iv)
iv) eluting the anthocyanin derivatives of step iii) from the adsorbent material for recovering the anthocyanin derivatives.

According to an embodiment, the homogenized extract is obtained by mixing and pulverizing the plant source in an polar acidified solvent. Preferably, the plant source is from a *vaccinium* fruit, such as lowbush blueberries.

According to an embodiment, the adsorbent material may be chosen from C-18 silica gel, or C-8 silica gel. Preferably, the adsorbent material is C-18 silica gel.

According to an embodiment, the method for extracting and purifying anthocyanin derivatives from a source of blueberries comprises the step of mixing a source of blueberries with an acidified polar solvent. The polar acidified solvent may be, without limitations, ethanol, methanol, ethyl acetate, water, acetone, butanol, or combinations, containing phosphoric acid, HCl, lactic acid, tartaric acid, citric acid and the like. The ratio of the source of blueberries on acidified solvent may be from about 1:4 to about 1:20 and more preferably, the ratio is about 1:10.

The step of mixing may occur, without limitations, in a reactor, a mixer or the like. The mixture, or the extract, is agitated at room temperature (about 21° C.), and/or pulverized, for a certain amount of time, and more specifically, for about 2 hours.

The solid/liquid mixture obtained at the end of the extraction period is filtered. The first filtration may occur on a press-filter, or on any other type of filter having a porosity of about 100 μm.

A residual solid and the filtrate containing the active substances dissolved in the solvent used for extraction are collected.

Solid (i.e. insoluble substances in the solvent) is dried for obtaining the residual solvent and water. This solid contains a non-negligible quantity of proteins and complex sugars that are mostly not soluble and poor in fat and simple sugars.

The liquid filtrate obtained is filtered another time on a cartridge filter, or any other type of filter having a porosity of about 10 μm for removing the fine insoluble particles.

The filtrate is afterward evaporated under a reduced pressure. The evaporation temperature is fixed to be slightly inferior to the ebullition temperature of the solvent that needs to be evaporated.

Once the solvent is eliminated from the filtrate (and residual water), a semi-solid extract containing the extractable substances and the anthocyanins is recuperated.

The extract obtained is dissolved in water. The obtained solution may be filtered and is placed at the head of a Solid Phase Extraction column, or SPE column, for allowing the separation of the anthocyanins through solid phase extraction. Alternatively, the extract could be processed using a batch process without a column.

The SPE column may be constituted of a cylindrical tube of a glass material and may have an internal volume of about 1.6 L.

Preferably, the adsorbent material is a C-18 type adsorbent which is introduced in the SPE column after dispersion in ethanol. The C-18 type adsorbent may be a modified silica gel, or any other suitable C-18 type adsorbent.

After the sedimentation of the gel at the bottom of the column, the residual solvent is eluted at the bottom of the SPE column by gravity.

The gel is then conditioned by eluting ethanol (95%) and demineralised water at a volumic flow of about 25 ml/minute in the SPE column, to clean and humidify the gel. The solvent elution may be achieved at atmospheric pressure (by gravity) or under an external pressure (between 0.1 and 1 Bar) according to the desired volumic flow.

The plant source extract dissolved in water is then introduced at the head of the SPE column. Water is slowly eluted and the adsorbed extract lies on the gel for a certain amount of time, preferably for one hour.

A first wash with water is accomplished by circulating water in the SPE column at a volumic flow of about 50 mL/min. This first wash allows the elution of sugars and inorganic substances present in the extract with the elution solvent. The other substances, comprising the anthocyanins, remain adsorbed on the gel.

A second wash is optional. This second wash may be accomplished with a second elution solvent such as hexane for removing waxes and fatty substances (triglycerides) from the extract. The other substances, comprising the anthocyanins, remain adsorbed on the silica gel.

A third wash is also optional. This third wash may be accomplished with a third elution solvent such as ethyl acetate for removing the neutral flavonoids from the extract. The other substances, comprising the anthocyanins, remain adsorbed on the silica gel.

Two successive washes of the gel are then accomplished with ethanol 95% in water: a wash with 1.5 L; and a wash with 0.5 L. This step allows desorption of anthocyanins from the silica gel. The elution volumic flow needed is about 25 ml/min.

For recuperating under a solid from the anthocyanin concentrated in solution in ethanol, the two ethanol fractions collected are combined and evaporated under reduced pressure.

Since between 1 and 5% by weight of residual solvent remains after the first evaporation of the solvent, the residual solvent is then separated from the collected solid by evaporation under high vacuum (<1 mbar).

According to another embodiment, to obtain an anthocyanins concentrate containing a higher anthocyanins concentration (e.g.: higher than 40%) the extract/gel ratio may be between 1:5 and 1:10, instead of 1:2.5. According to another embodiment, there is also a possibility to use a gradient of water/ethanol, for example a gradient from 30% ethanol in water to 95% ethanol in water.

The present invention will be more readily understood by referring to the following examples which are given to illustrate the invention rather than to limit its scope.

Example 1

Preparation of an Anthocyanin Concentrate (>38%)

One embodiment of the method for extracting and purifying anthocyanin derivatives from a source of blueberries comprises the step of mixing 8.5 kg of frozen blueberries (87% water) with 85 L of a polar solvent, i.e. ethanol (95%) containing 0.01% of phosphoric acid (ratio solid/liquid 1:10) in a double wall 100 L reactor. The mixture, or the extract, is agitated with an agitator/pulveriser at 800 rpm for 2 hours at room temperature (about 21° C.). The solid/liquid mixture obtained at the end of the extraction period is filtered on a press-filter having a porosity of about 100 μm. A residual solid and the filtrate containing the active substances dissolved in the solvent used for extraction are collected.

Solid (i.e. insoluble substances in the solvent) is dried for obtaining the residual solvent and water. This solid contains a non-negligible quantity of proteins and complex sugars that are mostly not soluble and poor in fat and simple sugars. The solid also has a theoretical energy of 5 kcal/g. Thus, the solid is a good source of energy in nutrition. 300 g of the solid are obtained (3.5% of the initial mass of source of blueberries).

The liquid filtrate obtained is filtered another time on a cartridge filter having a porosity of 10 μm for removing the fine insoluble particles. The filtrate is afterward evaporated under a reduced pressure. The evaporation temperature is fixed at 65° C., which is slightly inferior to the ebullition temperature of the solvent that needs to be evaporated. Once the solvent is eliminated from the filtrate (and residual water), a semi-solid extract containing the extractable substances and the anthocyanins is recovered. 800 g of dry extract are obtained, which corresponds to 9.4% of the initial mass of the source of blueberries.

A fraction of the extract obtained, 100 g of extract, is dissolved in 1 L of water. The obtained solution is filtrated and is placed at the head of a Solid Phase Extraction column, or SPE column, for allowing the separation of the anthocyanins through solid phase extraction.

The SPE column is constituted of a cylindrical tube of a glass material and has an internal volume of about 1.6 L.

400 g of a C-18 type adsorbent (i.e.: 0.8 L) obtained from CiliCycle inc. (Quebec, Canada) are introduced in the SPE column after dispersion in 0.8 L of ethanol (95%). The C-18 type adsorbent is a modified silica gel. The distribution of its particles is 40-63 μm, the organic charge is 0.38 mmol/g and the carbon charge is 9.16%.

After the sedimentation of the gel at the bottom of the column, the residual solvent is eluted at the bottom of the SPE column by gravity. It is to be noted that a small volume of liquid needs to be conserved on the gel in the SPE column for avoiding the gel to dry and to provide air gaps in the adsorbent material.

The gel is then conditioned by eluting 0.8 L of ethanol (95%) and 0.8 L of demineralised water at a volumic flow of 25 ml/minute in the SPE column. The solvent elution may be achieved at atmospheric pressure (by gravity) or under an external pressure (between 0.1 and 1 Bar) according to the desired volumic flow.

The blueberry extract dissolved in 1 L of water is then introduced at the head of the SPE column. Water is slowly eluted and the adsorbed extract lies on the gel for 1 hour.

A first wash with water is accomplished by letting circulate 2 L of water in the SPE column at a volumic flow of 25 mL/min. This first wash allows the elution of sugars and inorganic substances (90 g) present in the extract. The other substances, comprising the anthocyanins, remain adsorbed on the gel.

A second wash is optional. This second wash is accomplished with 1 L of hexane for pulling out waxes and fatty substances (triglycerides) from the extract (2 g). The other substances, comprising the anthocyanins, remain adsorbed on the silica gel.

A third wash is also optional. This third wash is accomplished with 1 L of ethyl acetate for removing the neutral flavonoids from the extract (1 g). The other substances, comprising the anthocyanins, remain adsorbed on the silica gel.

Two successive washes of the gel are then accomplished with 95% ethanol in water: a wash with 1.5 L; and a wash with 0.5 L. This step allows desorption of anthocyanins from the silica gel. The elution volumic flow needed is about 25 ml/min.

For recuperating under a solid form the anthocyanin concentrated in solution in ethanol, the two ethanol fractions collected are combined and evaporated under reduced pressure at a temperature slightly inferior to the ebullition temperature of the solvent that needs to be evaporated (65° C.).

Since between 1 and 5% by weight of residual solvent is obtained after the first evaporation of the solvent, the residual solvent is then separated from the collected solid by evaporation at vacuum pressure (>1 mbar). 6.5 g of concentrated anthocyanins are obtained at a concentration higher than 40%. The obtained yield is 0.61% compared to the frozen initial mass of blueberries source. The concentrate is a fine powder of a blue color and is mainly soluble in water.

Example 2

Temperature Variation for Homogenization

|  | Assay 1 | Assay 2 | Assay 3 | Assay 4 | Assay 5 |
| --- | --- | --- | --- | --- | --- |
| Initial grinding | No | Yes | Yes | No | No |
| Blueberry weight | 300 g | 300 g | 300 g | 300 g | 300 g |
| Solvent | ethanol 95% | ethanol 95% | ethanol 95% | ethanol 95% | ethanol 95% |
| Solvent volume | 3000 mL | 3000 mL | 2940 mL | 2940 mL | 2940 mL |
| Solid/solvent ratio | 1:10 | 1:10 | 1:10 | 1:10 | 1:10 |
| Agitation | 3000 rpm | 200 rpm | 3000 rpm | 3000 rpm | 3000 rpm |
| Agitation type | homogenizer | Screw | homogenizer | homogenizer | homogenizer |
| Temperature | 6° C. | 78° C. | 26° C. | 22° C. | 24° C. |
| Length | 2 h | 2 h | 2 h | 2 h | 2 h |
| Acid Added | None | None | HCl, 0.0004% | Tartaric Acid, 0.0004% | None |
| Filter | 25 μm | 25 μm | 25 μm | 25 μm | 25 μm |
| Extracted weight | 41.29 g | 36.1 g | 36.91 g | 29.89 g | 33.7 g |
| Yield | 13.8% | 12% | 12.3% | 10% | 11.2% |

Example 3

Variation of Solid/Solvent Ratio

|  | Assay 6 | Assay 7 | Assay 8 | Assay 9 |
| --- | --- | --- | --- | --- |
| Initial grinding | Yes | Yes | Yes | Yes |
| Blueberry weight | 750 g | 500 g | 375 g | 300 g |
| Solvent | ethanol 95% | ethanol 95% | ethanol 95% | ethanol 95% |
| Solvent volume | 3000 mL | 3000 mL | 3000 mL | 3000 mL |
| Solid/solvent ratio | 1:4 | 1:6 | 1:8 | 1:10 |
| Agitation | 3000 rpm | 3000 rpm | 3000 rpm | 3000 rpm |
| Agitation type | homogenizer | homogenizer | homogenizer | homogenizer |
| Temperature | 24° C. | 23° C. | 25° C. | 26° C. |
| Length | 2 h | 2 h | 2 h | 2 h |
| Acid Added | None | None | None | None |
| Filter | 25 μm | 25 μm | 25 μm | 25 μm |
| Extracted weight | 81.2 g | 54.9 g | 42.3 g | 34.2 g |
| Yield | 10.8% | 11% | 11.3% | 11.4% |

Example 4

Ethanol/Ethyl Acetate Mix

|  | Assay 10 |
| --- | --- |
| Initial grinding | No |
| Blueberry weight | 375 g |
| Solvent | Ethanol/ethyl acetate 80:20 |
| Solvent volume | 3000 mL |
| Solid/solvent ratio | 1:8 |
| Agitation | 3000 rpm |
| Agitation type | homogenizer |
| Temperature | 25° C. |
| Length | 2 h |
| Acid Added | None |
| Filter | 25 μm |
| Extracted weight | 42.7 g |
| Yield | 11.4% |

Example 5

Alcool/Water Mix

|  | Assay 11 | Assay 12 | Assay 13 | Assay 14 |
| --- | --- | --- | --- | --- |
| Initial grinding | Yes | Yes | Yes | Yes |
| Blueberry weight | 375 g | 375 g | 375 g | 375 g |
| Solvent | ethanol/water 70:30 | ethanol/water 50:50 | methanol/water 70:30 | ethanol/water 70:30 |
| Solvent volume | 2900 mL | 3000 mL | 3000 mL | 3000 mL |
| Solid/solvent ratio | 1:8 | 1:8 | 1:8 | 1:8 |
| Agitation | 3000 rpm | 3000 rpm | 3000 rpm | 3000 rpm |
| Agitation type | homogenizer | homogenizer | homogenizer | homogenizer |
| Temperature | 25° C. | 30° C. | 22° C. | 28° C. |
| Length | 2 h | 2 h | 2 h | 2 h |
| Acid Added | None | None | Phosphoric acid, 0.02% | Phosphoric acid, 0.02% |
| Filter | 25 μm | 25 μm | 25 μm | 25 μm |
| Extracted weight | 42 g | 42.4 g | 42.9 g | 41.5 g |
| Yield | 11.2% | 11.3% | 11.4% | 11.1% |

Example 6

Acetone, Ethyl Aceate, Water Solvent Testing

|  | Assay 15 | Assay 16 | Assay 17 | Assay 18 |
| --- | --- | --- | --- | --- |
| Initial grinding | Yes | Yes | Yes | Yes |
| Blueberry weight | 300 g | 300 g | 215 g | 300 g |
| Solvent | acetone | ethyl acetate | acetone/water 80:20 | acetone/water 85:15 |
| Solvent volume | 1500 mL | 1500 mL | 1500 mL | 1500 mL |
| Solid/solvent ratio | 1:5 | 1:5 | 1:7 | 1:5 |
| Agitation | 200 rpm | 200 rpm | 200 rpm | 200 rpm |
| Agitation type | screw | screw | screw | screw |
| Temperature | 25° C. | 22° C. | 22° C. | 25° C. |
| Length | 2 h | 2 h | 2 h | 2 h |
| Acid Added | None | None | None | None |
| Filter | 25 μm | 25 μm | 25 μm | 25 μm |
| Extracted weight | 30.1 g | 0.7 g | 22.8 g | 32.5 g |
| Yield | 10% | 0.2% | 10.6% | 10.8% |

Example 7

Temperature, Ethanol and Citric Acid

|  | Assay 19 | Assay 20 | Assay 21 |
| --- | --- | --- | --- |
| Initial grinding | Yes | Yes | Yes |
| Blueberry weight | 300 g | 300 g | 215 g |
| Solvent | ethanol 95% | ethanol 95% | ethanol 95% |
| Solvent volume | 3000 mL | 3000 mL | 3000 mL |
| Solid/solvent ratio | 1:10 | 1:10 | 1:10 |
| Agitation | 3000 rpm | 3000 rpm | 3000 rpm |
| Agitation type | homogenizer | homogenizer | homogenizer |
| Temperature | 22° C. | 78° C. | 10° C. |
| Length | 2 h | 2 h | 2 h |
| Acid Added | citric acid 0.0004% | citric acid 0.0004% | citric acid 0.0004% |
| Filter | 25 μm | 25 μm | 25 μm |
| Extracted weight | 29.1 g | 29.6 g | 26.27 g |
| Yield | 9.9% | 9.9% | 8.8% |

Example 8

Ethanol/Methanol and Phosphoric Acid

|  | Assay 22 | Assay 23 | Assay 24 | Assay 25 |
|---|---|---|---|---|
| Initial grinding | Yes | Yes | Yes | Yes |
| Blueberry weight | 200 g | 200 g | 200 g | 200 g |
| Solvent | ethanol 95% | ethanol 95% | ethanol 95% | Methanol |
| Solvent volume | 2000 mL | 2000 mL | 2000 mL | 3000 mL |
| Solid/solvent ratio | 1:10 | 1:10 | 1:10 | 1:8 |
| Agitation | 200 rpm | 200 rpm | 200 rpm | 3000 rpm |
| Agitation type | screw | screw | screw | homogenizer |
| Temperature | 80° C. | 79° C. | 79° C. | 22° C. |
| Length | 2 h | 2 h | 2 h | 2 h |
| Acid Added | phosphoric acid 0.01% | phosphoric acid 0.01% | phosphoric acid 0.01% | phosphoric acid 0.02% |
| Filter | 25 μm | 25 μm | 25 μm | 25 μm |
| Extracted weight | 22.3 g | 21.3 g | 24.8 g | 44.7 |
| Yield | 11.2% | 10.6% | 12.4% | 11.9% |

Example 9

Ethanol 95% and Room Temperature

|  | Assay 26 |
|---|---|
| Initial grinding | No |
| Blueberry weight | 8500 g |
| Solvent | ethanol 95% |
| Solvent volume | 85000 mL |
| Solid/solvent ratio | 1:10 |
| Agitation | 1200 rpm |
| Agitation type | homogenizer |
| Temperature | 18° C. |
| Length | 2 h |
| Acid Added | Phosphoric acid 0.01% |
| Filter | Press filter 100 μm and 20 μm cartridge |
| Extracted weight | 454800 g |
| Yield | 9.4% |

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for extracting anthocyanins from a plant source, comprising the steps of:
   i) separating an homogenized extract of said plant source in a polar solvent different than water for obtaining a residual solid and a filtrate, said filtrate containing residual water mixed with said polar solvent different than water; and
   ii) substantially separating said polar solvent different than water from said filtrate of step i) while substantially retaining said residual water, said separating being performed to obtain a semi-solid extract of anthocyanins.

2. The method as claimed in claim 1, wherein said polar solvent different than water is acidified.

3. The method as claimed in claim 1, wherein step i) comprises a coarse filtration performed using a step selected from:
   a centrifugation of said homogenized extract of said plant source,
   a filtration of said homogenized extract of said plant source with a first filter, or
   a combination thereof.

4. The method as claimed in claim 1, wherein step ii) is performed by evaporating said filtrate mixed with said polar solvent different than water of step i).

5. The method as claimed in claim 3, wherein said step i) further comprises a fine filtration performed by a second filter.

6. The method as claimed in claim 1, further comprising an anthocyanins purification step iii):
   iii) performing a solid phase extraction of said semi-solid extract of step ii) with an adsorbent material and a first elution solvent to adsorb said anthocyanins present in said semi-solid extract on said adsorbent material.

7. The method as claimed in claim 6, further comprising the step of:
   eluting said adsorbed anthocyanins of step iii) from said adsorbent material for recovering said purified anthocyanins.

8. The method of claim 1, wherein said plant source is a source of *vaccinium* fruit.

9. The method of claim 6, wherein said adsorbent material is selected from the group consisting of C-18 silica gel or C-8 silica gel.

10. The method of claim 1, wherein said homogenized extract of said plant source is obtained by mixing and pulverizing said plant source in said polar solvent different than water.

11. The method of claim 6, wherein step iii) includes washing said adsorbent material with said first elution solvent for eluting sugars and inorganic substances from said semi-solid extract.

12. The method of claim 1, wherein said polar solvent different than water is selected from the group consisting of ethanol, methanol, ethyl acetate, acetone, butanol or combinations thereof.

13. The method of claim 1, wherein said polar solvent different than water further comprises an acid selected from the group consisting of phosphoric acid, HCl or combinations thereof.

14. The method of claim 13, wherein said polar solvent different than water is 95% ethanol acidified with phosphoric acid.

15. The method of claim 1, wherein said homogenized extract is obtained at a temperature from about 6° C. to an ebullition temperature of said polar solvent different than water while agitating at a frequency of rotation between about 200 and to about 3000 RPM.

16. The method of claim 1, further comprising a step prior to step i) of cooling said homogenized extract before said separating.

17. The method of claim 4 wherein said evaporating operates at an evaporation temperature inferior to an ebullition temperature of said polar solvent different than water.

18. The method of claim 6, wherein said first elution solvent is water or demineralized water.

19. The method of claim 6, further comprising a step prior to step iii) of dissolving in water said semi-solid extract and filtrating said semi-solid extract dissolved in water.

20. The method of claim 7, wherein said recovering said purified anthocyanins is performed using an elution solution of about 95% ethanol in water or a gradient from 30% ethanol in water to 95% ethanol in water.

21. A method for extracting and purifying anthocyanins from a plant source, comprising the steps of:
   i) separating an homogenized extract of said plant source in an acidified polar solvent different than water for obtaining a residual solid, and a filtrate containing residual water mixed with said acidified polar solvent different than water;
   ii) evaporating under reduced pressure said filtrate mixed with said acidified polar solvent different than water of step i) for substantially separating said acidified polar solvent different than water from said filtrate while substantially retaining said residual water to obtain a semi-solid extract of anthocyanins;
   iii) performing a solid phase extraction of said semi-solid extract of step ii) with an adsorbent material and a first elution solvent to adsorb said anthocyanins present in said semi-solid extract on said adsorbent material; and
   iv) eluting said adsorbed anthocyanins of step iii) from said adsorbent material with a third elution solvent for recovering said purified anthocyanins.

22. A method for extracting anthocyanins from a filtrate containing residual water mixed with a polar solvent different than water used for separating an homogenized extract of a plant source into said filtrate and a residual solid, said method comprising the step of substantially separating said polar solvent different than water from said filtrate while substantially retaining said residual water to obtain a semi-solid extract of anthocyanins.

23. A method for extracting anthocyanins from a plant source containing at least about 87% w/w water, comprising the steps of:
   i) separating an homogenized extract of said plant source in a polar solvent different than water for obtaining a residual solid, and a filtrate containing residual water mixed with said polar solvent different than water; and
   ii) substantially separating said polar solvent different than water from said filtrate of step i) while substantially retaining said residual water, to obtain a semi-solid extract of anthocyanins.

24. The method of claim 4, wherein said evaporating is performed under reduced pressure.

25. The method of claim 6, wherein a ratio of adsorbent material/extract is from about 1:1 to about 10:1.

26. The method of claim 9, wherein said C-18 adsorbent silica gel has a particle distribution of about 40 to about 63 µm.

27. The method of claim 9, wherein said C-18 adsorbent silica gel has an organic charge of about 0.38 mmol/g.

28. The method of claim 9, wherein said C-18 adsorbent silica gel has a carbon charge of about 9.16%.

29. The method of claim 9, wherein a ratio C-18 adsorbent silica gel/extract is about 2.5:1.

30. The method of claim 11, wherein step iii) further comprises washing said adsorbent material with a second elution solvent for eluting waxes and fatty substances from said extract.

31. The method of claim 11, wherein step iii) further comprises washing said adsorbent material with a third elution solvent for eluting neutral flavonoids from said extract.

32. The method of claim 11, wherein said elution first solvent is water, and wherein said second elution solvent is hexane, and wherein said third elution solvent is ethyl acetate.

33. The method of claim 12, wherein said polar solvent different than water further comprises water.

* * * * *